United States Patent [19]

Wu et al.

[11] Patent Number: 6,081,116

[45] Date of Patent: Jun. 27, 2000

[54] NUCLEAR MAGNETIC RESONANCE APPARATUS AND METHOD FOR GEOLOGICAL APPLICATIONS

[75] Inventors: Jian-Qun Wu, Houston; Macmillan M. Wisler, Kingwood, both of Tex.

[73] Assignee: Baker Hughes Incorporated, Houston, Tex.

[21] Appl. No.: 09/063,773

[22] Filed: Apr. 21, 1998

Related U.S. Application Data

[60] Provisional application No. 60/044,088, Apr. 21, 1997.

[51] Int. Cl.[7] .................................................. G01V 3/00
[52] U.S. Cl. ......................... 324/303; 324/307; 324/300; 600/410
[58] Field of Search .................................. 324/303, 307, 324/300; 600/410

[56] References Cited

U.S. PATENT DOCUMENTS

| | | |
|---|---|---|
| 3,617,867 | 11/1971 | Herzog . |
| 4,350,955 | 9/1982 | Jackson et al. . |
| 4,629,986 | 12/1986 | Clow et al. . |
| 4,710,713 | 12/1987 | Strikman . |
| 4,714,881 | 12/1987 | Givens ..................................... 324/303 |
| 4,717,876 | 1/1988 | Masi et al. ............................... 324/303 |
| 4,933,638 | 6/1990 | Kenyon et al. . |
| 5,212,447 | 5/1993 | Paltiel . |
| 5,280,243 | 1/1994 | Miller ...................................... 324/303 |
| 5,309,098 | 5/1994 | Coates et al. . |
| 5,517,115 | 5/1996 | Prammer . |
| 5,557,201 | 9/1996 | Kleinberg et al. ....................... 324/303 |
| 5,629,623 | 5/1997 | Sezginer et al. . |
| 5,757,186 | 5/1998 | Taicher et al. ........................... 324/303 |
| 5,831,433 | 11/1998 | Sezginer et al. ........................ 324/303 |

*Primary Examiner*—Christine K. Oda
*Assistant Examiner*—Brij Shrivastav
*Attorney, Agent, or Firm*—Madan, Mossman & Sriram P.C.

[57] ABSTRACT

The present invention provides a nuclear magnetic resonance ("NMR") tool for determining geological properties of formations surrounding a borehole when said tool is traversed in the borehole. One embodiment of the NMR tool includes at least one permanent magnet that is disposed substantially parallel to a longitudinal axis of the tool to generate a static magnetic field at a known distance in the formation. Radio frequency magnetic field in the zone of interest is generated by passing current at a radio frequency through a linear electrical conduction path along the longitudinal axis of the tool. The frequency may be swept during operation of the tool. The return path for the RF current is through the formation. A receiver detects signals from the formation responsive to the induced radio frequency magnetic field, which are processed to provide information about a formation parameter such as the formation porosity, hydrocarbon saturation and permeability of the zone of interest. A plurality of symmetrically arranged permanent magnets may be utilized instead of a single permanent magnet. An alternative embodiment utilizes a plurality of permanent magnets to produce a static magnetic field that is substantially radial in the zone of interest.

35 Claims, 5 Drawing Sheets

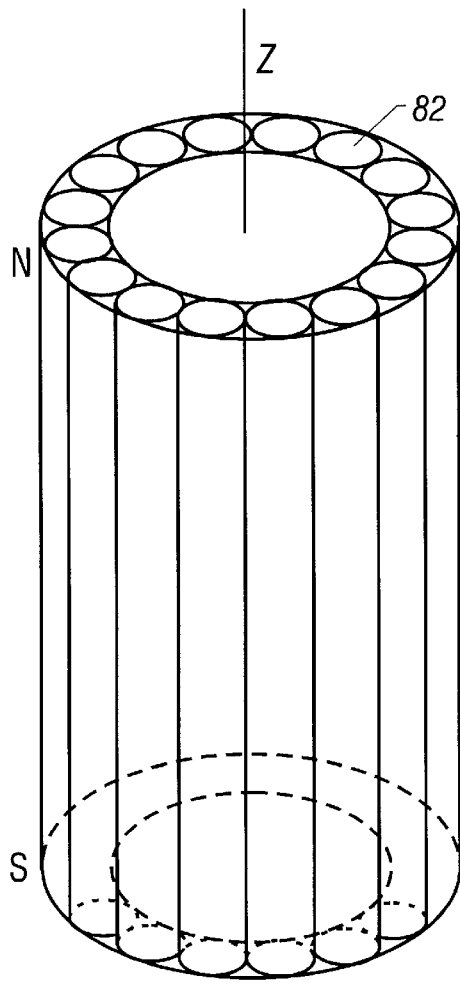 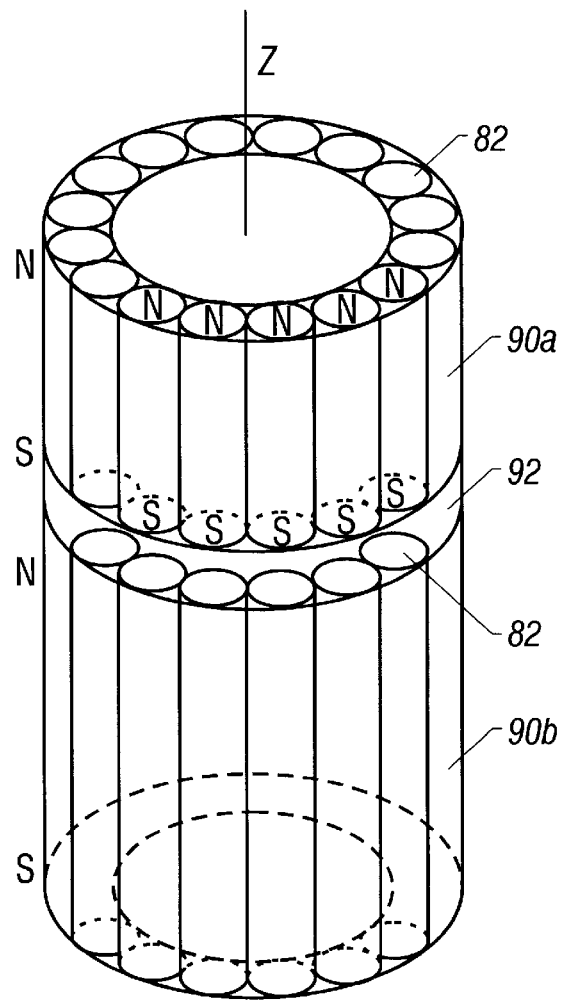
FIG. 3A  FIG. 3B

NUCLEAR MAGNETIC RESONANCE APPARATUS AND METHOD FOR GEOLOGICAL APPLICATIONS

REFERENCES TO RELATED APPLICATIONS

This application claims priority from Provisional U.S. Patent Application Ser. No. 60/044,088 filed on Apr. 21, 1997.

BACKGROUND OF THE INVENTION

1. Field of the Invention

This invention relates generally to determining geological properties of subsurface formations and more particularly to Nuclear Magnetic Resonance ("NMR") apparatus and methods for logging wellbores, particularly for obtaining information relating to the presence of hydrocarbons in such formations.

2. Background of the Art

A variety of techniques have are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling of the wellbores, which is referred to as measurement-while-drilling "MWD" or logging-while-drilling ("LWD").

One recently evolving technique involves utilizing Nuclear Magnetic Resonance (NMR) logging tools and methods for determining, among other things porosity, hydrocarbon saturation and permeability of the rock formations. The NMR logging tools are utilized to excite the nuclei of the of the liquids in the geological formations surrounding the wellbore so that certain parameters such as spin density, longitudinal relaxation time (generally referred to in the art as "$T_1$") and transverse relaxation time (generally referred to as "$T_2$") of the geological formations can be measured. From such measurements, porosity, permeability and hydrocarbon saturation are determined, which provides valuable information about the make-up of the geological formations and the amount of extractable hydrocarbons.

The NMR tools generate a constant or near constant static magnetic field in a region of interest surrounding the wellbore. A radio frequency (RF) signal is induced in the formation to generate an alternating magnetic field which is perpendicular or near perpendicular to the static magnetic field in the region of interest to perturb the nuclei. The perturbation is measured to determine the parameters of interest.

The NMR logging tools typically utilize a magnetic source such as specially configured permanent magnets to generate the desired static magnetic field and one or more coils to generate the corresponding perpendicular RF magnetic field in the region of interest around the borehole.

Examples of prior art NMR logging tools and methods can be found in the following U.S. Pat. No. 3,508,438 (Alger et al.), U.S. Pat. No. 3,617,867 (Herzog), U.S. Pat. No. 3,667,035 (Slichter), U.S. Pat. No. 4,350,955 (Jackson), U.S. Pat. No. 4,467,642 (Givens), U.S. Pat. No. 4,528,508 (Vail), U.S. Pat. No. 4,560,663 (Nicksic et al.), U.S. Pat. No. 4,629,986 (Clow et al.), U.S. Pat. No. 4,710,713 (Strikman), U.S. Pat. No. 4,713,881 (Givens), U.S. Pat. No. 4,933,638 (Kenyon et al.), U.S. Pat. No. 4,717,876 (Masi et al.), U.S. Pat. No. 5,212,447 (Paltiel), U.S. Pat. No. 5,280,243 (Miller), U.S. Pat. No. 5,309,098 (Coates, et al.) and U.S. Pat. No. 5,517,115 (Prammer).

Most of the above-noted and other prior art logging tools utilize relatively complex permanent magnet and RF signal coils combinations. Furthermore, most of these tools are designed for wireline logging, i.e, for logging boreholes after they have been drilled. The formation evaluation MWD tools must operate in much harsher environments compared to wireline logging tools. This is primarily because the MWD tools are disposed in the drill string above the drill bit and, thus, must withstand high radial and axial vibrations. Furthermore, MWD tools rotate as the drill string rotates, which in prior art NMR tools tends to cause the static magnetic field to vary in the zone of interest, thereby decreasing signal to noise ratio and thus, the quality of the measurements. The Miller patent discloses an NMR apparatus that is designed for MWD applications. However, the disclosed apparatus still utilizes relatively complex magnet and coil structures.

Many of the prior art logging tools tend to utilize magnets to impart magnetic field that extends radially outward from the longitudinal axis of the tool and the borehole, and loop antennas for generating RF magnetic field which is perpendicular (orthogonal) to the static magnetic field. These types of structures tend to lead to relatively complex designs whose static magnetic field is affected due to the rotation of the tool during MWD applications. Prior art tools also usually require large areas of non-conducting material around the RF antennas. These non-conducting materials generally have a lower mechanical strength than conducting materials, a drawback in MWD applications.

The present invention addresses some of the above-noted problems with the prior art NMR logging tool and provides NMR logging tools wherein the RF antennas are linear, i.e., along the tool longitudinal direction, and one or more permanent magnets disposed along the tool longitudinal axis, primarily with their north and south poles along the tool longitudinal direction.

SUMMARY OF THE INVENTION

The present invention provides a nuclear magnetic resonance ("NMR") tool for determining geological properties of formations surrounding a borehole when said tool is traversed in the borehole. The NMR tool includes at least one permanent magnet that is disposed substantially parallel to a longitudinal axis of the tool to generate a static magnetic field at a known distance in the formation. The static magnetic field is azimuthally symmetrical and has components in the z and ρ directions of a cylindrical coordinate system. An RF magnetic field in the zone of interest is generated by forcing a sheet of current in the longitudinal direction (linear electrical conduction path along the longitudinal axis of the tool) at a known frequency. The frequency may be swept during operation of the tool. A receiver detects signals from the formation that are responsive to the induced radio frequency magnetic field. These signals are processed to determine one or more formation parameters such as porosity, type of fluid, hydrocarbon saturation and permeability of the zone of interest. The permanent magnet may include a plurality of permanent magnets symmetrically arranged around the tool.

The present invention provides a method for determining geological properties of interest of formations surrounding a borehole by inducing nuclear magnetic resonance in the formation by a logging tool whose longitudinal axis is along the borehole. The method comprises: (a) inducing a substantially constant static magnetic field in the direction of the longitudinal axis or in a radial direction; (b) inducing an RF magnetic field by passing RF current through a conductor disposed substantially colinear to the longitudinal axis; (c) measuring the response of the formation to the induced RF magnetic field; and (d) processing the measured response to determine the properties of the geological properties of interest of the formation. One of the novel features of the present invention is that the current in the antenna is in the longitudinal direction of the tool with a return path through the formation.

Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

BRIEF DESCRIPTION OF THE DRAWINGS

For a detailed understanding of the present invention, references should be made to the following detailed description of the preferred embodiment, taken in conjunction with the accompanying drawings, in which like elements have been given like numerals, wherein:

FIG. 3A shows an elevational view of an arrangement of permanent magnets for use in the NMR tool of the present invention.

FIG. 3B shows an elevational view of an alternative arrangement of permanent magnets for use in the NMR tool of the present invention.

DETAILED DESCRIPTION OF PREFERRED EMBODIMENTS

Figure 1:
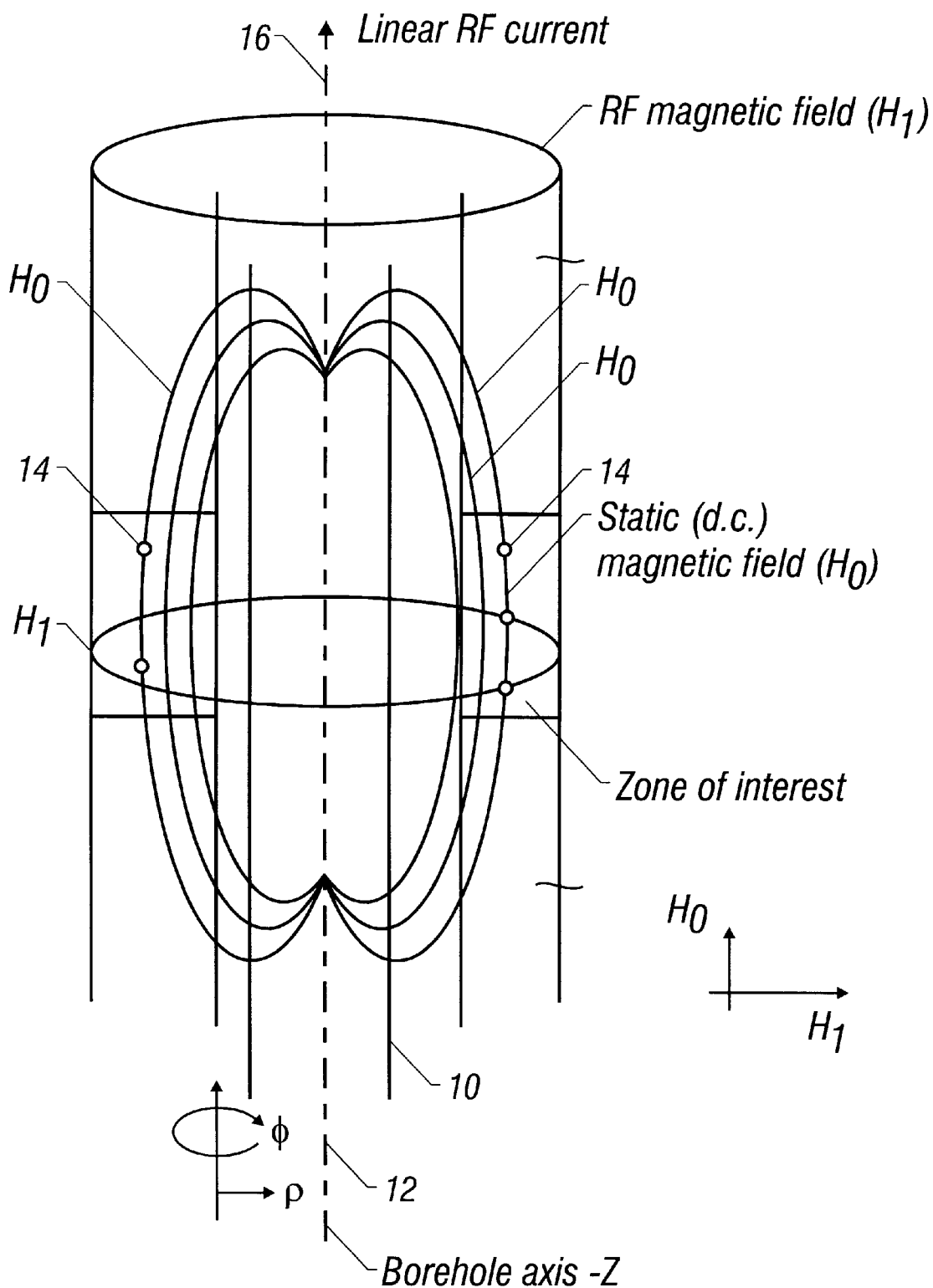
FIG. 1 shows a schematic illustration of an elevational view of the relationship of the static or d.c. and RF magnetic fields relative to the borehole and tool longitudinal axes utilized in the NMR logging tool of the present invention.

FIG. 1 shows a schematic illustration of an elevational view of the relationship of the static or d.c. and RF magnetic fields relative to the borehole and tool longitudinal axes utilized in one embodiment of the NMR logging tool of the present invention. FIG. 1 shows a borehole 10 with a longitudinal axis or z-axis 12 and a zone of interest (formation) 14 surrounding the borehole 10. During operations, the logging tools traverse the borehole along the z-axis 12. NMR principles require the generation of a constant or near constant static or d.c. magnetic field in the zone of interest and a corresponding RF magnetic field perpendicular to the static magnetic field in the zone of interest. The RF signal frequency is selected based upon the strength of the static magnetic field in the zone of interest and the desired depth of investigation.

Still referring to FIG. 1, in the present invention, a constant or substantially constant static magnetic field $H_0$ is induced which is azimuthally symmetrical and has direction in the z and $\rho$ directions of a cylindrical coordinate system. A corresponding RF magnetic field $H_1$ which is perpendicular to the z direction (static magnetic field $H_0$) is generated by forcing a sheet of current 16 in the longitudinal direction 12 (also referred herein as the "linear RF current"). The linear RF current 16 passes along the entire length of the zone of interest, thereby creating an RF magnetic field $H_1$ that is perpendicular to the z-axis throughout the zone of interest. The static magnetic field $H_0$ substantially symmetrical around the borehole 10 and is preferably generated by suitably placed permanent magnets in the tool, as described later in reference to FIGS. 2–4. The return path for the RF current is through the formation.

Figure 2:
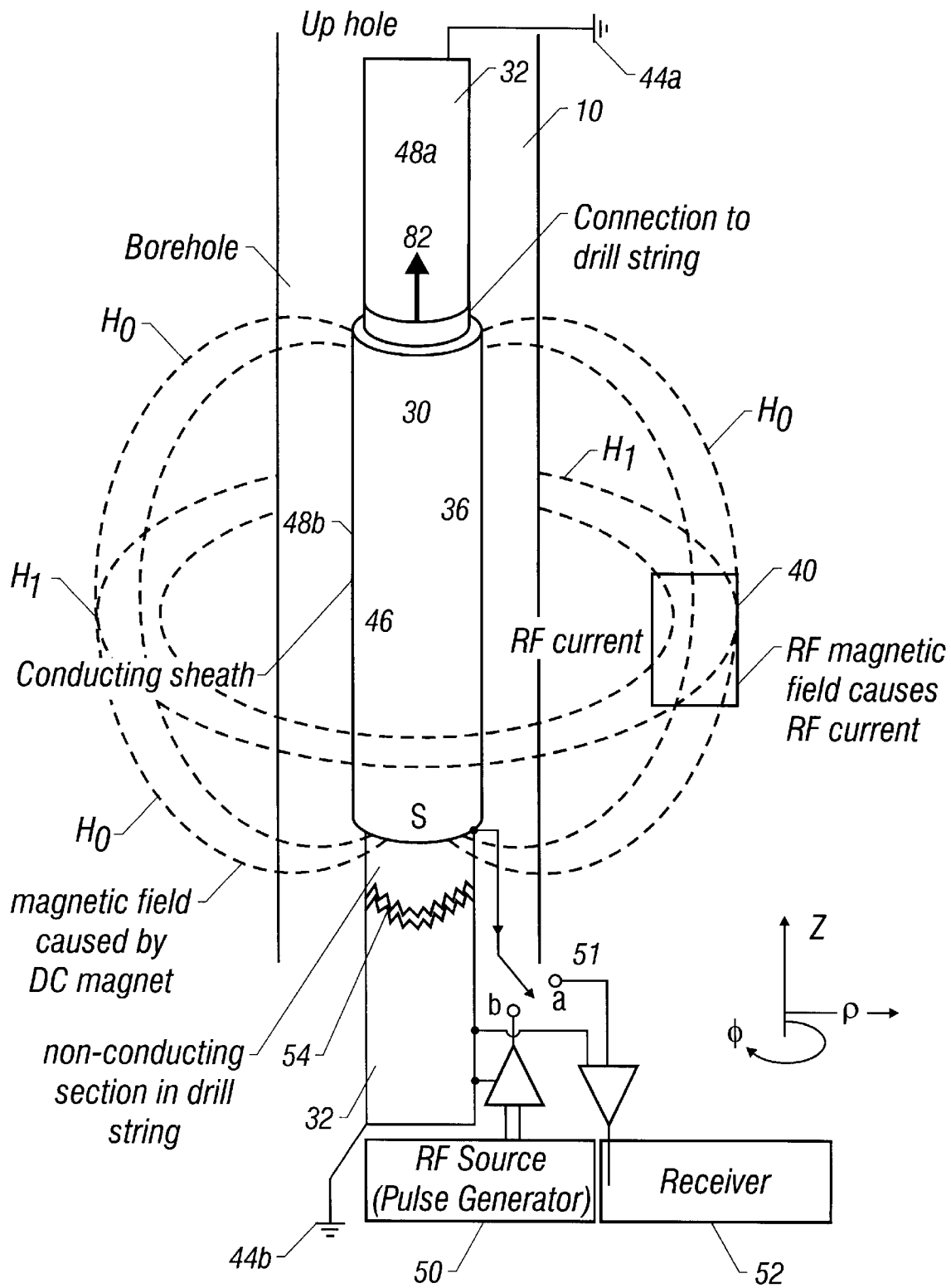
FIG. 2 shows a schematic elevational illustration of an NMR logging tool according to the present invention.

FIG. 2 shows a schematic elevational illustration of an NMR logging tool 30 according to the present invention along with the relationship of the static and RF magnetic fields. The NMR tool 30 is shown as an MWD tool. The concepts and the tool described herein are equally applicable to other NMR applications, including wireline logging applications. The NMR tool 30 is disposed in a drill string 32, which has a drill bit at its downhole end (not shown). The NMR tool 30 preferably is a part of a bottomhole assembly, which may contain any number of other formation evaluation devices, such as resistivity devices, acoustic devices and nuclear devices, and any number of other devices, such as a mud motor, stabilizers, direction control devices and steering devices. The use of such other devices and sensors is known in the art. For simplicity and not as limitation, such devices are not shown or described herein.

Still referring to FIG. 2, the NMR logging tool 30 includes a magnet arrangement, discussed below with reference to FIGS. 3–4, that is linearly disposed in the tool 30 so as to induce a constant static magnetic field $H_0$ in the zone of interest 40 at a predetermined median distance "d" from the tool axis 36. The static magnetic field so generated is azimuthally symmetrical and has components in the z and $\rho$ directions of a cylindrical coordinate system as shown in FIG. 2. The magnet arrangement preferably comprises one or more permanent magnets as more fully described later in reference to FIGS. 3A, 3B and 3C. Any suitable permanent magnet, including ones made from materials such as samarium cobalt having a high remanent magnetization may be utilized for the purposes of the NMR logging tool 30 of the present invention. An RF magnetic field $H_1$ is generated by passing or forcing linear RF current 46 via a conducting sheet (which may be a wire or conducting sheet around the drill string 32) disposed along the z-axis. The conducting sheet is connected to the drill string at a suitable point 56. One or more non-conducting sections, such as section 54 are provided in the drill string. The drillstring above and below the NMR tool is effectively connected to ground potential via the mud to the formation, denoted by 44a and 44b. The RF current is caused to flow along the drill pipe by placing the switch 51 in the "b" position. The return RF current flows through the formation via the symbolic ground connections 44a and 44b. The linear conductor is generally denoted herein by numeral 48. A pulse generator 50 may be utilized to pass the required current at a desired frequency through the linear conductor 48. The RF frequency is selected based on the static magnetic field strength in the zone of interest 40. A range of frequencies may be selected for various depths of investigation. The pulse generator 50 may be used to sweep the frequencies in one or more ranges of frequencies.

During operations, the NMR tool 30, whether in the wireline mode or in the MWD environment travels along the borehole 10. The magnet 34 induces a constant static magnetic field in the zone of interest 40 mainly in the z-direction. The RF source 50 passes electric current through the linear conductor 48 at a known frequency, which in turn induces a corresponding RF magnetic field $H_1$ perpendicular to the static magnetic field $H_0$. The RF magnetic field $H_1$ perturbs the nuclei of the fluids in the zone of interest 40, which generates a response signal. Switch 51 is moved to the "a" position and receiver 52 detects the response signals, which are processed by methods known in the art to determine the parameters of interest, including porosity, hydrocarbon saturation and permeability of the rock matrix in the zone of interest 40.

The NMR tool or system 30 of the present invention preferably utilizes a downhole computer (microprocessor) and other digital and analog circuits for signal processing. Such circuits are known in the art and are, thus, not described herein. It will, however, be understood that any suitable circuits, devices and programs may be utilized for processing the signals in the tool 30.

FIG. 3A shows an elevational view of an arrangement of permanent magnets for use in the NMR tool 30 (FIG. 2) of the present invention for generating substantially constant static magnetic field in a zone of interest around a borehole. In one embodiment, the magnet arrangement 80 may include a number of individual permanent magnets 82 symmetrically disposed axially (parallel to the z-axis) to form a cylinder 84. Similar poles of all such magnets are all oriented in the same direction. Thus, the north pole of all magnets 82 are in one direction and the south pole of all magnets are on the opposite direction. The individual magnets 82 may be embedded in a non-magnetic material or otherwise disposed around a suitable material. The individual magnets 82 may be equally spaced apart. In an alternative embodiment as shown in FIG. 3B, more that one cylindrical configurations of the magnets 82 such as shown by cylinders 90a and 90b may be disposed along the axial direction, with the opposite poles facing adjacent cylinder ends. For example, the north pole of the cylinder 90a faces uphole while the south pole faces downhole. The north pole of the cylinder 90b faces the south pole of the cylinder 90a. A suitable gap 92 may be provided between adjacent cylinders. Any number of cylinders or segments may be utilized, with or without any gaps, such as gaps 92, depending upon the zone or zones of interest and the depth of investigation desired. Gaps can also be used to substantially increase the reluctance of the magnetic circuit. High mu materials may be used in the gaps. In the region of interest 40, the static magnetic field is substantially longitudinal in direction and orthogonal to the RF magnetic field.

In an alternate embodiment of the invention, the permanent magnet assembly is used to produce a static field $H_0$ that has a region of constant field strength 40 in which the field direction is radial, i.e., in the ρ-direction. As discussed above, the RF field $H_1$ is in an azimuthal direction, so that the static and RF fields are still orthogonal to each other, a necessary condition for making NMR measurements. This radial magnetic field is produced by a magnet arrangement as shown in FIG. 3C. Shown are a two sets of outer cylindrical magnets 94a, 94b. However, unlike the arrangement shown in FIG. 3C, these magnets have their directions of magnetization opposed. For example, the magnets in 94a have north poles to the top and the magnets in 94b have their north poles to the bottom. As would be known to those versed in the art, this arrangement of matched magnets produces a toroidal region of substantially uniform magnetic field strength midway between the magnets 94a and the magnets 94b centered on the longitudinal axis of the assembly. The direction of the magnetic field in this region is radial, i.e., orthogonal to the longitudinal axis of the assembly. This radial static field is still orthogonal to the RF magnetic field, a prerequisite for making NMR measurements.

Figure 3C:
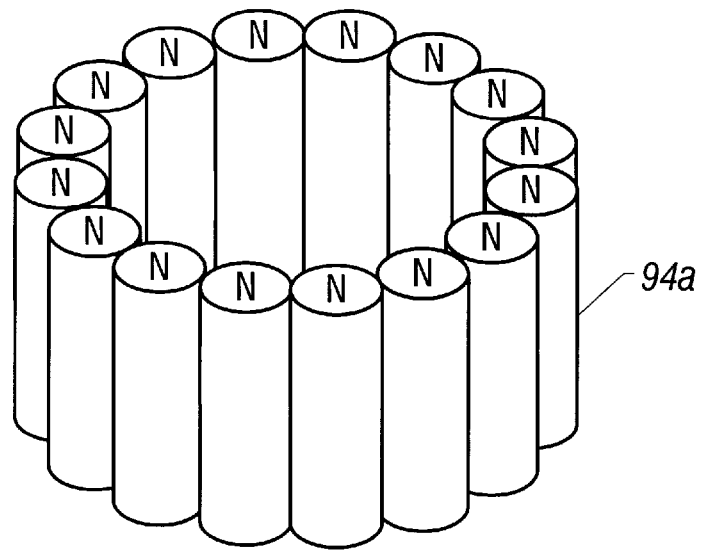
FIG. 3C shows a view of an alternative arrangement of permanent magnets for use in the NMR tool of the present invention that produces a radial static field.
Figure 3C:
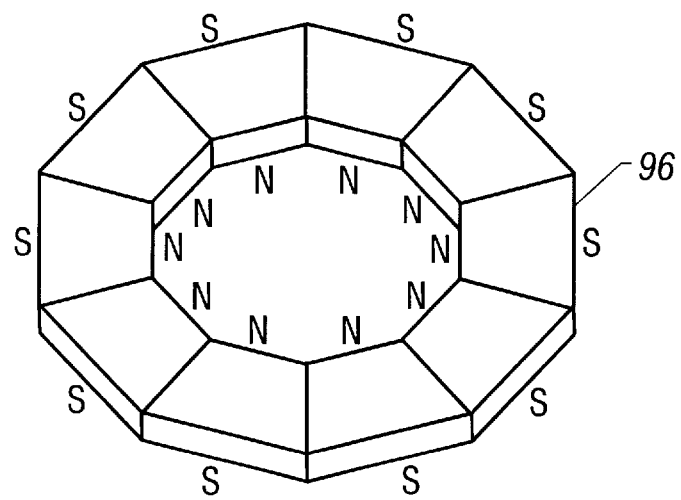
Figure 3C:
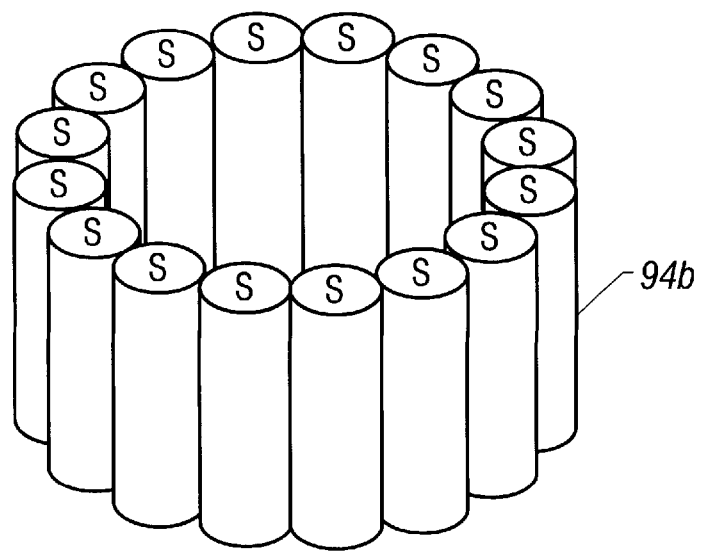

FIG. 3C also shows a second set of inner magnets 96 interposed between the outer magnets 94a, 94b. The inner magnets are radially magnetized, and, in the example shown, have north poles on the inside (close to the axis) and south poles on the outside. This arrangement helps to shape the zone of substantially constant field strength 40. Additionally, high mu materials may be used in the gaps between the sets of magnets to further shape the region 40.

Figure 4:
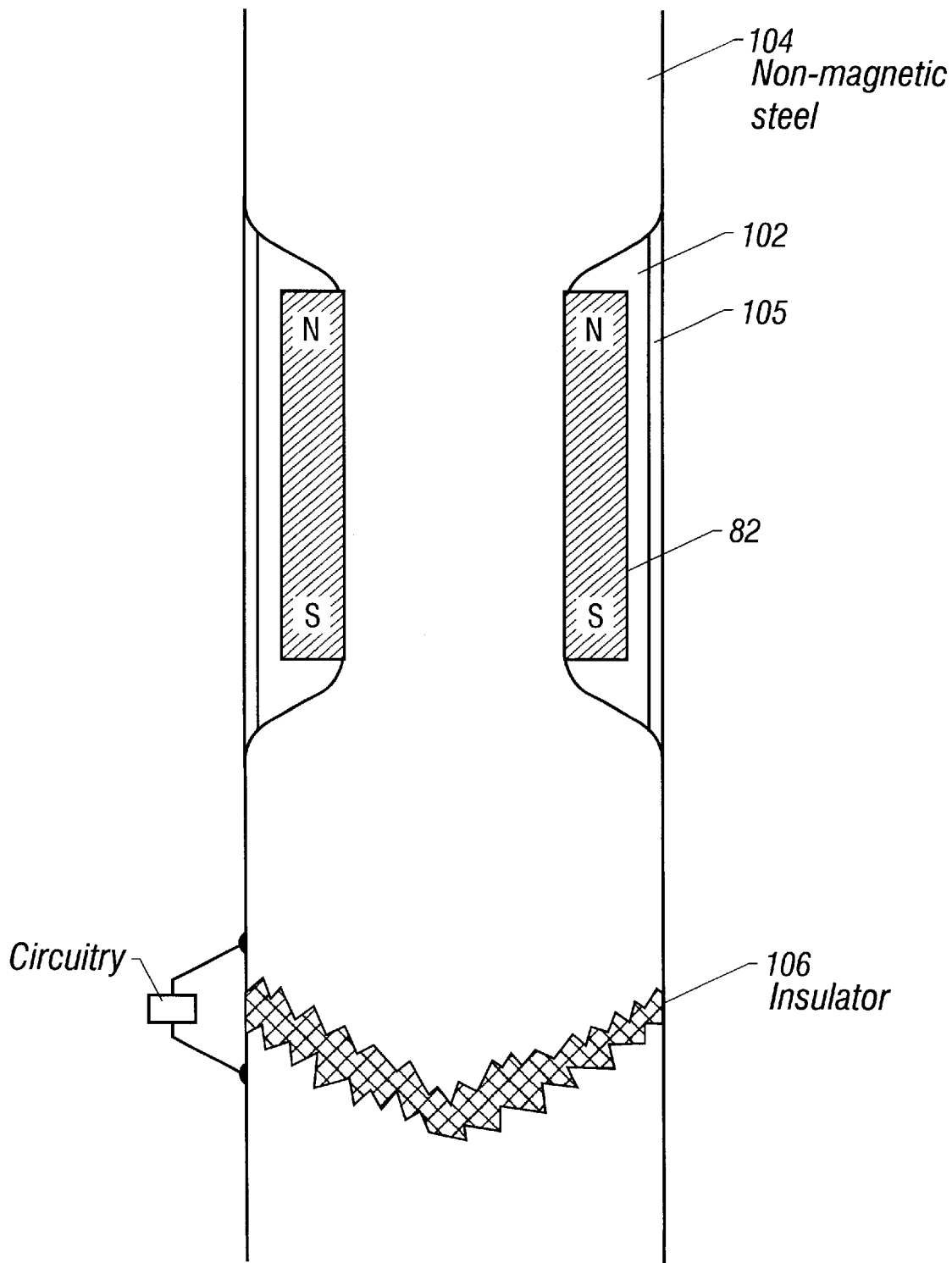
FIG. 4 shows a manner of placing permanent magnets in a tubular arrangement for use in the NMR logging tool of the present invention.

FIG. 4 shows a method of placing the permanent magnets 82 shown in FIGS. 3A and 3B in a tool suitable for MWD applications. The illustration shows the arrangement of magnets 82 but the same arrangement may be used with the magnets 94 and 96 in FIG. 3C. Permanent magnets 82 may be embedded or placed in a non-magnetic casing 102 disposed in a non-magnetic steel housing 104. A conducting outer layer 105 is provided exterior to the magnet. A suitable insulator 106 may be placed at a desired distance from the permanent magnets 82. The required circuitry, including the RF circuitry 110 may be disposed in the steel housing 104. The placement of such circuits in MWD tools is known in the art and is, thus, not described in detail here. Instead of multiple individual permanent magnets 82, a single cylindrical permanent magnet may be disposed in the manner described above.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A nuclear magnetic resonance apparatus, having a longitudinal axis, for determining a property of interest of a material a certain distance from the tool, comprising:
   (a) a magnet assembly operative to generate a static magnetic field in the material; and
   (b) a source for generating a radio frequency (RF) magnetic field in the material substantially perpendicular to the static magnetic field in the material for exciting nuclei in said material, said RF source passing current at a frequency along the longitudinal direction of the tool to generate the radio frequency magnetic field in the material wherein said current has a return path through the material.

2. The apparatus of claim 1, wherein the magnet assembly comprises a permanent magnet that generates the static magnetic field in a direction that is substantially parallel to the longitudinal axis of the tool.

3. The apparatus according to claim 1, wherein the magnet assembly comprises a plurality of permanent magnets disposed symmetrically around a periphery of the apparatus parallel to the longitudinal axis of the apparatus.

4. The apparatus according to claim 1, wherein the source for generating the RF magnetic field includes a conductor disposed linearly relative to the longitudinal axis of the apparatus.

5. The apparatus according to claim 1, wherein the source of RF magnetic field is adapted sweep frequencies within a range of frequencies.

6. The apparatus according to claim 3, wherein the plurality of permanent magnets are disposed within a non-magnetic material placed along a non-magnetic material housing.

7. The apparatus of claim 1, wherein the static magnetic field is in a direction that is substantially orthogonal to the longitudinal axis of the tool.

8. The apparatus of claim 7, wherein the magnet assembly comprises a first plurality of cylindrical magnets having an axis of magnetization parallel to said longitudinal axis, half of said plurality of magnets having a first direction of magnetization being disposed on a first side of a central plane orthogonal to said longitudinal axis and half of said plurality of magnets having a direction of magnetization opposite the first direction being disposed on a second side of the central plane opposite the first side.

9. The apparatus of claim 8 wherein the magnet assembly further comprises a second plurality of magnets having a direction of magnetization orthogonal to said longitudinal axis.

10. A nuclear magnetic resonance tool for determining a property of interest in a zone of interest of a formation surrounding a borehole when said tool is traversed in the borehole, said tool having a longitudinal axis along the borehole, said tool comprising:
   (a) a permanent magnet assembly to generate a static magnetic field in the zone of interest substantially parallel to the longitudinal direction; and
   (b) a device for generating radio frequency (RF) magnetic field in the zone of interest and for detecting echos, said device comprising:
      (i) a linear electrical conductor which is substantially parallel to the longitudinal axis so that when electrical current at a radio frequency is passed through the linear electrical conductor, an alternating magnetic field is generated that is substantially perpendicular to the static magnetic field generated by the permanent magnet; and
      (ii) a source for inducing electrical current into the linear electrical conductor.

11. The nuclear magnetic resonance tool according to claim 10, wherein the permanent magnet assembly comprises a plurality of permanent magnets disposed symmetrically around a periphery of the tool and substantially parallel to the longitudinal axis of the apparatus.

12. The nuclear magnetic resonance tool according to claim 10, wherein the permanent magnet assembly comprises at least two sets of permanent magnets disposed linearly along the longitudinal axis o the tool, wherein each set includes a plurality of individual permanent magnets disposed symmetrically around a periphery of the tool.

13. The nuclear magnetic resonance tool according to claim 10, wherein the device for generating the RF magnetic field is adapted sweep frequencies within a range of frequencies.

14. The apparatus according to claim 12, wherein the at least two sets of permanent magnets are disposed within a non-magnetic material placed along a non-magnetic material housing.

15. A nuclear magnetic resonance tool for determining a property of interest in a zone of interest of a formation surrounding a borehole when said tool is traversed in the borehole, said tool having a longitudinal axis along the borehole, said tool comprising:
   (a) a permanent magnet assembly to generate a static magnetic field in the zone of interest substantially orthogonal to the longitudinal direction; and
   (b) a device for generating radio frequency (RF) magnetic field in the zone of interest and for detecting echos, said device comprising:
      (i) a linear electrical conductor which is substantially parallel to the longitudinal axis so that when electrical current at a radio frequency is passed through the linear electrical conductor, an alternating magnetic field is generated that is substantially perpendicular to the static magnetic field generated by the permanent magnet; and
      (ii) a source for inducing electrical current into the linear electrical conductor.

16. A method for determining a parameter of interest of a formation surrounding a borehole, said method comprising
   (a) conveying in the borehole an apparatus having a longitudinal axis comprising:
      (i) a magnet assembly, and
      (ii) a source of electrical current;
   (b) using the magnet assembly to produce a static magnetic field having a substantially constant field strength in a zone in the formation, said static field further having a direction in said zone;
   (c) using the source to flow a Radio Frequency (RF) current in the longitudinal direction of the apparatus, said RF current having a return path through the formation, thereby inducing an RF magnetic field in said zone and exciting the nuclei therein, said RF magnetic field being orthogonal to said direction of the static magnetic field; and
   (d) receiving a signal from said excited nuclei.

17. The method of claim 16, wherein said direction of the static magnetic field is substantially parallel to the longitudinal axis of the apparatus.

18. The method of claim 16, wherein the current in the tool passes through a conductor disposed linearly relative to the longitudinal axis of the apparatus.

19. The method of claim 16, wherein said direction of the static magnetic field is substantially orthogonal to the longitudinal axis of the apparatus.

20. The method of claim 16, wherein the magnet assembly comprises a plurality of permanent magnets disposed symmetrically around a periphery of the apparatus parallel to the longitudinal axis of the apparatus.

21. The method of claim 16, wherein the magnet assembly comprises a first plurality of cylindrical magnets having an axis of magnetization parallel to said longitudinal axis, half of said plurality of magnets having a first direction of magnetization being disposed on a first side of a central plane orthogonal to said longitudinal axis and half of said plurality of magnets having a direction of magnetization opposite the first direction being disposed on a second side of the central plane opposite the first side.

22. A measurement-while-drilling (MWD) nuclear magnetic resonance (NMR) tool for use on a drillstring conveyed in a borehole, said tool having a longitudinal axis and further comprising:
   (a) a permanent magnet assembly to generate a static magnetic field in a formation surrounding the borehole;
   (b) a device adapted for passing a radio frequency (RF) electrical current in the tool parallel to said longitudinal axis and inducing an RF magnetic field in the formation, said RF current having a return path through the formation; and
   (c) a device adapted for detecting NMR signals excited in the formation by said RF magnetic field.

23. The MWD tool of claim 22 further comprising a non-conducting section interposed between the tool and the drillstring.

24. The MWD tool of claim 22 wherein the permanent magnet assembly is located inside a nonmagnetic casing.

25. The MWD tool of claim 24 further comprising a conducting layer exterior to the permanent magnet assembly.

26. A nuclear magnetic resonance apparatus having a longitudinal axis, for determining a property of a material in a zone of interest, comprising:

(a) a magnet assembly operative to generate a static magnetic field in the zone of interest, said static field aligning nuclear spins of the material in the zone of interest substantially parallel to a direction of said static field;

(b) a transmitter for generating a radio frequency (RF) magnetic field in the material, said RF field having a direction substantially perpendicular to the static magnetic field in the zone of interest for exciting nuclei in said material and;

(c) a substantially linear receiver antenna oriented parallel to said longitudinal axis receiving induced signals from the excited nuclei.

27. The apparatus according to claim 26, wherein the magnet assembly comprises a plurality of permanent magnets disposed symmetrically around a periphery of the apparatus parallel to the longitudinal axis of the apparatus.

28. The apparatus according to claim 26, wherein the transmitter includes a conductor disposed linearly relative to the longitudinal axis of the apparatus.

29. The apparatus according to claim 27, wherein the plurality of permanent magnets are disposed within a non-magnetic material placed along a non-magnetic material housing.

30. The nuclear magnetic resonance tool according to claim 26, wherein the transmitter is adapted sweep frequencies within a range of frequencies.

31. A method for determining a parameter of interest of a formation surrounding a borehole, said method comprising (a) using a magnet assembly on an apparatus conveyed in the borehole for producing a static magnetic field having a direction in a zone of interest in the formation;

(b) using a transmitter on the apparatus for inducing a Radio Frequency (RF) magnetic field in said zone, the RF magnetic field having a direction orthogonal to said direction of the static magnetic field in the zone of interest, thereby exciting nucleii in the zone; and (c) using a receiver having a substantially linear antenna for receiving a signal from said excited nuclei.

32. The method of claim 31, wherein the magnet assembly comprises a plurality of permanent magnets disposed symmetrically around a periphery of the apparatus parallel to a longitudinal axis of the apparatus.

33. A measurement-while-drilling (MWD) nuclear magnetic resonance (NMR) tool for use on a drillstring conveyed in a borehole, said tool having a longitudinal axis and further comprising:

(a) a permanent magnet assembly to generate a static magnetic field in a zone of interest in a formation surrounding the borehole;

(b) a device adapted for inducing an RF magnetic field in the zone of interest, said RF magnetic field having a direction in the zone of interest substantially orthogonal to a direction of the static field; and (c) a substantially linear receiver antenna adapted for detecting NMR signals excited in the zone of interest by said RF magnetic field.

34. The MWD tool of claim 33 further comprising a non-conducting section interposed between the tool and the drillstring.

35. The MWD tool of claim 33 wherein the permanent magnet assembly is located inside a nonmagnetic casing.

* * * * *